United States Patent
Debain et al.

(10) Patent No.: US 8,088,173 B2
(45) Date of Patent: Jan. 3, 2012

(54) COMPOSITION FOR OXIDATION DYEING OF HUMAN KERATIN FIBERS, AT A PH GREATER THAN OR EQUAL TO 8, COMPRISING A FATTY ALCOHOL, A FATTY ESTER AND A CATIONIC SURFACTANT, METHOD USING SAME AND DEVICE

(75) Inventors: Jean-Daniel Debain, Bezons (FR); Bruno Laguitton, Kremlin Bicetre (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/743,095

(22) PCT Filed: Nov. 14, 2008

(86) PCT No.: PCT/FR2008/052056
§ 371 (c)(1),
(2), (4) Date: Feb. 11, 2011

(87) PCT Pub. No.: WO2009/068830
PCT Pub. Date: Jun. 4, 2009

(65) Prior Publication Data
US 2011/0126363 A1 Jun. 2, 2011

(30) Foreign Application Priority Data
Nov. 15, 2007 (FR) .................................. 07 59069

(51) Int. Cl.
*A61Q 5/10* (2006.01)

(52) U.S. Cl. ............. 8/405; 8/406; 8/408; 8/410; 8/411; 8/412; 8/435; 8/580; 8/611; 132/202; 132/208

(58) Field of Classification Search ............... 8/405, 406, 8/408, 410, 411, 435, 580, 611; 132/202, 132/208
See application file for complete search history.

(56) References Cited

U.S. PATENT DOCUMENTS

| 7,169,193 | B2 | 1/2007 | Kleen et al. |
| 7,553,338 | B2 | 6/2009 | Weser et al. |
| 2004/0172771 | A1 * | 9/2004 | Cottard et al. ................... 8/405 |
| 2008/0216252 | A1 | 9/2008 | Cottard et al. |

FOREIGN PATENT DOCUMENTS

| DE | 199 14 926 A1 | 2/2000 |
| DE | 100 20 887 A1 | 10/2001 |
| DE | 10 2004 062 702 A1 | 3/2006 |
| EP | 1 426 039 A1 | 6/2004 |
| WO | WO 2005/063179 A1 | 7/2005 |

OTHER PUBLICATIONS

International Search Report for PCT/FR2008/052056, dated Mar. 1, 2010.
English language abstract of DE 199 14 926 A1, Feb. 24, 2000.

* cited by examiner

*Primary Examiner* — Eisa Elhilo
(74) *Attorney, Agent, or Firm* — Finnegan, Henderson, Farabow, Garrett & Dunner

(57) ABSTRACT

The present invention relates to a dye composition for the oxidation dyeing of human keratin fibers, at a pH greater than or equal to 8, comprising at least one oxidation dye precursor, at least one fatty alcohol, at least one fatty ester and at least one cationic surfactant, where the weight ratio of the at least one fatty alcohol and the at least one fatty acid ester being greater than 2 and less than 10. In addition, the present invention relates to a ready-to-use composition obtained by extemporaneously mixing the dye composition with an oxidizing composition, before use, and a method for dyeing keratin fibers in which the ready-to-use composition is applied to hair fibers.

17 Claims, No Drawings

COMPOSITION FOR OXIDATION DYEING OF HUMAN KERATIN FIBERS, AT A PH GREATER THAN OR EQUAL TO 8, COMPRISING A FATTY ALCOHOL, A FATTY ESTER AND A CATIONIC SURFACTANT, METHOD USING SAME AND DEVICE

This application is a National Stage application under 35 U.S.C. §371 of International Application No. PCT/FR2008/052056, filed Nov. 14, 2008, and claims the benefit of priority of French Application No. 0759069, filed Nov. 15, 2007, the content of each of which is incorporated herein by reference.

The present invention relates to a dyeing composition for the oxidative dyeing of human keratin fibres, at a pH greater than or equal to 8, comprising one or more oxidative dye precursors, one or more fatty alcohols and fatty esters as well as one or more cationic surfactants, a method of colouring keratin fibres in which said composition is applied on said fibres as well as a device with several compartments that are suitable for its application.

Among the methods of colouring human keratin fibres, such as the hair, we may mention oxidative or permanent colouring. More particularly, this method of colouring employs one or more oxidative dye precursors, more particularly one or more oxidation bases optionally combined with one or more couplers.

Oxidation bases are usually selected from the ortho- or para-phenylenediamines, the ortho- or para-aminophenols as well as the heterocyclic compounds. These oxidation bases are colourless or slightly coloured compounds which, combined with oxidizing products, make it possible to obtain coloured species, by a process of oxidative condensation.

Quite often, the shades obtained with these oxidation bases are varied by combining them with one or more couplers, the latter being selected notably from the aromatic meta-diamines, the meta-aminophenols, the meta-diphenols and certain heterocyclic compounds, such as indole compounds.

The variety of molecules constituting the oxidation bases and couplers makes it possible to obtain a rich palette of colours.

This method of colouring can also be combined with direct or semi-permanent dyeing. The method conventionally used in direct dyeing consists of applying, on the keratin fibres, direct dyes, which are coloured and colouring molecules, having affinity for the fibres, pausing to allow the molecules to penetrate, by diffusion, to the interior of the fibre, then rinsing.

The direct dyes generally used are selected from the nitrobenzene, anthraquinone, nitropyridine, azoic, methine, azomethine, xanthene, acridine, azine or triarylmethane direct dyes.

One of the drawbacks of the oxidative dyeing processes is the fact that the coloration of the composition applied on the fibres changes considerably between the start of application and when the composition is finally removed. This phenomenon, entirely conventional, is characteristic of the degree of progression of the aforementioned reaction of oxidative condensation, leading to the appearance of the coloured species.

However, depending on the shade chosen, the composition is of a more or less deep or more or less chromatic colour and does not always correspond perfectly to the final coloration of the hair, which the user may find annoying.

Moreover, the stronger the colour of the composition, the greater are the risks of marking of the skin and the scalp.

However, the more or less rapid appearance of the coloration of the composition also constitutes a drawback for the actual dyeing process. In fact, the polymer synthesized in the composition during the pause is not synthesized in the keratin fibre and this represents a decrease in the effectiveness of coloration. Consequently it is necessary to use larger amounts of dye precursors in order to compensate this loss of reagents, causing among other things an increase in cost of the composition.

Another drawback observed when employing methods of oxidative dyeing at pH greater than or equal to 8, is the effect of the presence of ammonia. This alkalizing agent is used not only for adjusting the pH of the dyeing composition but also for swelling the keratin fibre in order to promote the penetration of the dyes as well as of the oxidizing agent into the fibre, where the polycondensation takes place.

As this agent is very volatile, we observe a loss of ammonia, which is unfavourable for the method and is troublesome for the user owing to the strong, rather offensive characteristic odour of such compositions.

Therefore it is not purely and simply a matter of using less ammonia in these compositions, despite the risks of intolerance that may sometimes be observed at these concentrations (irritation of the scalp in the form of tingling).

One of the aims of the present invention is therefore to propose dyeing compositions that limit the aforementioned drawbacks connected with the appearance of the coloration of the composition during application and with the release of ammonia from the composition, when ammonia is present in the composition, but without adversely affecting the dyeing properties or the utility properties of such compositions.

It was in fact found, completely unexpectedly, that such results could be obtained by combining, in dyeing compositions employed at a pH greater than or equal to 8, one or more fatty alcohols, one or more fatty esters with one or more cationic surfactants.

In such conditions, it was found that the development of the coloration of the composition applied was slowed considerably during application, to the point that in certain cases the colour of the composition did not change substantially during the pause, even with a deep final coloration of the keratin fibres.

Moreover, this slowing of the rate of the reaction of oxidative condensation in the composition is, advantageously and unexpectedly, not a reflection of the rate of coloration within the keratin fibre itself, as it is not necessary to increase the duration of the pause to obtain the desired coloration of the fibres.

It should be noted that this development of the coloration of the composition is particularly visible when the composition only contains oxidative dyes. However, this phenomenon is always present when the composition includes one or more direct dyes, although it may be masked to a varying extent by the colour supplied by said direct dye or dyes.

The composition according to the invention therefore makes it possible to increase the efficiency of the method of colouring, in other words a larger amount of reagent is used effectively for colouring the fibre and not the composition, in contrast to the compositions used conventionally.

Moreover, this advantage is not achieved to the detriment of the other criteria measuring the efficiency of a dyeing composition, i.e. notably the intensity, homogeneity and chromaticity of the resultant coloration, which are still very good within the scope of the invention.

Thus, the composition according to the invention makes it possible, in order to obtain a level of coloration similar to that achieved when employing a conventional composition, to reduce the amount of dye to 20 wt. % relative to the amount used conventionally.

It was also observed that, unexpectedly, when ammonia is present in the composition, the amount of ammonia released from the composition was less than that released by usual compositions with the same ammonia content.

The compositions according to the invention therefore make it possible to limit the drawbacks due to the presence of ammonia, without the need to lower its concentration.

However, since it is possible to limit the release of ammonia, it would be entirely feasible to lower the ammonia content of the compositions without finding a drop in efficiency of coloration, which would normally be expected in such circumstances.

These and other aims are achieved by the present invention, which therefore relates to a composition (A) whose pH is greater than or equal to 8, for colouring human keratin fibres, in particular the hair, comprising, in a cosmetically acceptable medium:
   one or more precursors of oxidative dyes;
   one or more cationic surfactants;
   one or more fatty acid esters;
   one or more fatty alcohols;
   the weight ratio of fatty alcohol(s) to fatty acid ester(s) being greater than 2 and less than 10.

It also relates to a ready-to-use composition (B) whose pH is greater than or equal to 8 comprising one or more precursors of oxidative dyes, one or more cationic surfactants, one or more fatty acid esters, one or more fatty alcohols, one or more oxidizing agents. More particularly, said composition (B) is obtained by mixing an aforementioned dyeing composition (A) with an oxidizing composition such that said mixture has a pH greater than or equal to 8.

It also relates to a method of colouring human keratin fibres, in particular the hair, in which the ready-to-use composition is applied on the keratin fibres.

According to another variant of the method according to the invention, the aforementioned composition (A) and an oxidizing composition are applied successively, without intermediate rinsing.

Finally it relates to a device with several compartments containing in at least one first compartment, composition (A) according to the invention, and in at least one second compartment, a composition comprising one or more oxidizing agents.

Other characteristics and advantages of the invention will become clearer on reading the description and the examples given below.

It should be noted that in the following, and unless stated otherwise, the limits of a range of values are included in said range.

As already stated, the composition according to the invention includes one or more precursors of oxidative dyes, more particularly one or more oxidation bases optionally combined with one or more couplers.

As examples, the oxidation bases are selected from the paraphenylenediamines, the bis-phenylalkylenediamines, the para-aminophenols, the ortho-aminophenols, the heterocyclic bases and their salts of addition.

Among the paraphenylenediamines, we may mention, for example, paraphenylenediamine, paratoluoylenediamine, 2-chloro-paraphenylenediamine, 2,3-dimethyl paraphenylenediamine, 2,6-dimethyl paraphenylenediamine, 2,6-diethyl paraphenylenediamine, 2,5-dimethyl paraphenylenediamine, N,N-dimethyl paraphenylenediamine, N,N-diethyl paraphenylenediamine, N,N-dipropyl paraphenylenediamine, 4-amino-N,N-diethyl-3-methyl aniline, N,N-bis-(β-hydroxyethyl) paraphenylenediamine, 4-N,N-bis-(β-hydroxyethyl)amino-2-methyl aniline, 4-N,N-bis-(β-hydroxyethyl)amino-2-chloro-aniline, 2-(β-hydroxyethyl paraphenylenediamine, 2-fluoro paraphenylenediamine, 2-isopropyl paraphenylenediamine, N-(β-hydroxypropyl) paraphenylenediamine, 2-hydroxymethyl paraphenylenediamine, N,N-dimethyl-3-methyl paraphenylenediamine, N,N-(ethyl,β-hydroxyethyl) paraphenylenediamine, N-(β,γ-dihydroxypropyl) paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylene-diamine, 4-aminophenylpyrrolidine, 2-thienyl paraphenylenediamine, 2-β-hydroxyethylamino-5-aminotoluene, 3-hydroxy-1-(4'-aminophenyl)pyrrolidine and their salts of addition with an acid.

Among the paraphenylenediamines mentioned above, paraphenylenediamine, paratoluoylenediamine, 2-isopropyl paraphenylenediamine, 2-β-hydroxyethyl paraphenylenediamine, 2-β-hydroxyethyloxy paraphenylene-diamine, 2,6-dimethyl paraphenylenediamine, 2,6-diethyl paraphenylenediamine, 2,3-dimethyl paraphenylenediamine, N,N-bis-(β-hydroxyethyl)paraphenylenediamine, 2-chloro-paraphenylenediamine, 2-β-acetylaminoethyloxy paraphenylenediamine, and their salts of addition with an acid are particularly preferred.

Among the bis-phenylalkylenediamines, we may mention for example N,N'-bis-(β-hydroxyethyl) N,N'-bis-(4'-aminophenyl) 1,3-diaminopropanol, N,N'-bis-(β-hydroxyethyl) N,N'-bis-(4'-aminophenyl)ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl)tetramethylenediamine, N,N'-bis-(ethyl) N,N'-bis-(4'-amino, 3'-methylphenyl)ethylenediamine, 1,8-bis-(2,5-diaminophenoxy)-3,6-dioxaoctane, and their salts of addition.

Among the para-aminophenols, we may mention for example para-aminophenol, 4-amino-3-methyl phenol, 4-amino-3-fluorophenol, 4-amino-3-chlorophenol, 4-amino-3-hydroxymethyl phenol, 4-amino-2-methyl phenol, 4-amino-2-hydroxymethyl phenol, 4-amino-2-methoxymethyl phenol, 4-amino-2-aminomethyl phenol, 4-amino-2-(β-hydroxyethyl aminomethyl)phenol, 4-amino-2-fluorophenol, and their salts of addition with an acid.

Among the ortho-aminophenols, we may mention for example 2-aminophenol, 2-amino-5-methyl phenol, 2-amino-6-methyl phenol, 5-acetamido 2-aminophenol, and their salts of addition.

Among the heterocyclic bases, we may mention for example the pyridine derivatives, the pyrimidine derivatives and the pyrazole derivatives.

Among the pyridine derivatives, we may mention compounds described for example in patents GB 1 026 978 and GB 1 153 196, such as 2,5-diaminopyridine, 2-(4-methoxyphenyl)amino-3-aminopyridine, 3,4-diaminopyridine, and their salts of addition.

Other pyridine oxidation bases that can be used in the present invention are the 3-aminopyrazolo-[1,5-a]-pyridine oxidation bases or their salts of addition described for example in patent application FR 2801308. As examples, we may mention pyrazolo[1,5-a]pyridin-3-ylamine; 2-acetylaminopyrazolo-[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine;

pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; as well as their salts of addition.

Among the pyrimidine derivatives, we may mention the compounds described for example in patents DE 2359399; JP 88-169571; JP 05-63124; EP 0770375 or patent application WO 96/15765 such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their salts of addition and their tautomeric forms, when there is tautomeric equilibrium.

Among the pyrazole derivatives, we may mention compounds described in patents DE 3843892, DE 4133957 and patent applications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl pyrazole, 4,5-diamino-3-methyl-1-phenyl pyrazole, 4,5-diamino-1-methyl-3-phenyl pyrazole, 4-amino-1,3-dimethyl-5-hydrazino pyrazole, 1-benzyl 4,5-diamino-3-methylpyrazole, 4,5-diamino-3-tert-butyl 1-methyl pyrazole, 4,5-diamino-1-tert-butyl 3-methylpyrazole, 4,5-diamino-1-(β-hydroxyethyl) 3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl pyrazole, 4,5-diamino-3-methyl-1-isopropyl pyrazole, 4-amino-5-(2'-aminoethyl)amino 1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their salts of addition. 4-5-Diamino-1-(β-methoxyethyl) pyrazole can also be used.

As pyrazole derivatives we may also mention diamino-N,N-dihydropyazolones and notably those described in application FR 2886136 such as the following compounds and their salts of addition: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di-(2-hydroxyethyl)-1,2-dihydro-pyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydro-pyrazol-3-one, 4-amino-5-(3-dimethylamino-pyrrolidin-1-yl)-1,2-diethyl-1,2-dihydro-pyrazol-3-one, 2,3-diamino-6-hydroxy-6,7-dihydro-1H,5H-pyrazolo[1,2-a]pyrazol-1-one.

Preferably 4,5-diamino-1-(β-hydroxyethyl)pyrazole and/or 2,3-diamino-6,7-dihydro-1H,5H-pyrazolo[1,2,A]pyrazol-1-one and their salts of addition will be used as heterocyclic bases.

The composition according to the invention can optionally include one or more couplers selected advantageously from those conventionally used for the dyeing of keratin fibres.

Among these couplers, we may notably mention meta-phenylenediamines, meta-aminophenols, meta-diphenols, naphthalenic couplers, heterocyclic couplers as well as their salts of addition.

As examples, we may mention 1,3-dihydroxybenzene, 1,3-dihydroxy-2-methyl benzene, 4-chloro-1,3-dihydroxybenzene, 2,4-diamino-1-(β-hydroxyethyloxy)benzene, 2-amino-4-(β-hydroxyethylamino) 1-methoxybenzene, 1,3-diaminobenzene, 1,3-bis-(2,4-diaminophenoxy)propane, 3-ureido aniline, 3-ureido-1-dimethylamino benzene, sesamol, 1-β-hydroxyethylamino-3,4-methylenedioxybenzene, α-naphthol, 2-methyl-1-naphthol, 6-hydroxy indole, 4-hydroxy indole, 4-hydroxy N-methyl indole, 2-amino-3-hydroxy pyridine, 6-hydroxy benzomorpholine 3,5-diamino-2,6-dimethoxypyridine, 1-N-(β-hydroxyethyl)amino-3,4-methylene dioxybenzene, 2,6-bis-(β-hydroxyethylamino) toluene, 6-hydroxy indoline, 2,6-dihydroxy-4-methylpyridine, 1-H-3-methylpyrazol-5-one, 1-phenyl-3-methylpyrazol-5-one, 2,6-dimethyl pyrazolo[1,5-b]-1,2,4-triazole, 2,6-dimethyl[3,2-c]-1,2,4-triazole, 6-methyl pyrazolo[1,5-a]-benzimidazole, their salts of addition with an acid, and mixtures thereof.

In general, the salts of addition of the oxidation bases and of the couplers that can be used within the scope of the invention are notably selected from the salts of addition with an acid, such as the hydrochlorides, hydrobromides, sulphates, citrates, succinates, tartrates, lactates, tosylates, benzenesulphonates, phosphates and acetates.

The oxidation base or bases each represent advantageously from 0.0001 to 10 wt. % relative to the total weight of the composition, and preferably from 0.005 to 5 wt. % relative to the total weight of the composition.

The content of coupler(s), if present, each represent advantageously from 0.0001 to 10 wt. % relative to the total weight of the composition, and preferably from 0.005 to 5 wt. % relative to the total weight of the composition.

The composition according to the invention can also include one or more direct dyes. The latter are notably selected from the ionic or non-ionic species, preferably cationic or non-ionic.

As examples of suitable direct dyes, we may mention azo; methine; carbonyl; azine; nitro(hetero)aryl; tri-(hetero)arylmethane direct dyes; porphyrins; phthalocyanines and the natural direct dyes, alone or mixed.

More particularly, the azo dyes contain a function —N=N— whose two nitrogen atoms are not simultaneously incorporated in a ring. It is not excluded, however, that one of the two nitrogen atoms of the —N=N— chain is incorporated in a ring.

The dyes of the methine class are more particularly compounds comprising at least one sequence selected from >C=C< and —N=C< whose two atoms are not simultaneously incorporated in a ring. It is specified, however, that one of the nitrogen or carbon atoms in the sequences can be incorporated in a ring. More particularly, the dyes of this class are derived from compounds such as methine, azomethine, mono- and di-arylmethane, indoamines (or diphenylamines), indophenols, indoanilines, carbocyanines, azacarbocyanines and their isomers, diazacarbocyanines and their isomers, tetraazacarbocyanines, hemicyanines.

Regarding the dyes of the carbonyl class, we may mention for example the dyes selected from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, coumarin.

Regarding the dyes of the cyclic azine class, we may notably mention azine, xanthene, thioxanthene, fluorindine, acridine, (di)oxazine, (di)thiazine, pyronine.

The (hetero) aromatic nitro dyes are more particularly nitro-benzene or nitro-pyridine direct dyes.

Regarding the dyes of the porphyrin or phthalocyanine type, it is possible to use compounds that are cationic or otherwise, optionally including one or more metals or metal ions, for example alkali metals and alkaline-earth metals, zinc and silicon.

As examples of direct dyes that are particularly suitable, we may mention the nitro dyes of the benzene series; the azo; azomethine; methine direct dyes; the azacarbocyanines such as the tetraazacarbocyanines (tetraazapentamethines); the quinone and in particular anthraquinone, naphthoquinone or benzoquinone direct dyes; the azine; xanthene; triarylmethane; indoamino; indigoid direct dyes; phthalocyanines, porphyrins and the natural direct dyes, alone or mixed.

These dyes can be monochromophoric dyes (i.e. only containing a single dye) or polychromophoric, preferably di- or tri-chromophoric; the chromophores can be identical or different, of the same or different chemical classes. Note that a polychromophoric dye contains several radicals each derived from a molecule absorbing in the visible region between 400 and 800 nm. Moreover, said absorbance of the dye requires neither previous oxidation of the latter, nor combination with other chemical species.

In the case of polychromophoric dyes, the chromophores are joined together by at least one linkage, which can be cationic or otherwise.

Preferably, the linkage is a linear, branched or cyclic $C_1$-$C_{20}$ alkyl chain, optionally interrupted by at least one heteroatom (such as nitrogen, oxygen) and/or by at least one group containing them (CO, $SO_2$), optionally interrupted by at least one condensed or uncondensed heterocycle with a phenyl nucleus and comprising at least one quaternized nitrogen atom incorporated in said ring and optionally at least one other heteroatom (such as oxygen, nitrogen or sulphur), optionally interrupted by at least one substituted or unsubstituted phenyl or naphthyl group, optionally at least one quaternary ammonium group substituted with two $C_1$-$C_{15}$ alkyl groups, optionally substituted; the linkage not containing a nitro, nitroso or peroxo group.

If the heterocycles or aromatic nuclei are substituted, they are substituted for example with one or more $C_1$-$C_8$ alkyl radicals optionally substituted with a hydroxy group, $C_1$-$C_2$ alkoxy, $C_2$-$C_4$ hydroxyalkoxy, acetylamino, amino substituted with one or two $C_1$-$C_4$ alkyl radicals, optionally bearing at least one hydroxyl group or the two radicals can form, with the nitrogen atom to which they are attached, a heterocycle with 5 or 6 ring members, optionally including another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

Among the benzene direct dyes that can be used according to the invention, we may mention non-exhaustively the following compounds:
1,4-diamino-2-nitrobenzene,
1-amino-2-nitro-4-β-hydroxyethylaminobenzene
1-amino-2-nitro-4-bis(β-hydroxyethyl)-aminobenzene
1,4-bis(β-hydroxyethylamino)-2-nitrobenzene
1-β-hydroxyethylamino-2-nitro-4-bis-(β-hydroxyethylamino)-benzene
1-β-hydroxyethylamino-2-nitro-4-aminobenzene
1-β-hydroxyethylamino-2-nitro-4-(ethyl)(β-hydroxyethyl)-aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis-(β-hydroxyethylamino)-4-nitrobenzene
1-amino-2-tris-(hydroxymethyl)-methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
hydroxy-2-amino-4,6-dinitrobenzene-1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis-(β-hydroxyethyl)-amino-3-nitrobenzene
1-β-hydroxyethylamino-2-nitrobenzene
1-hydroxy-4-β-hydroxyethylamino-3-nitrobenzene.

Among the azo, azomethine, methine or tetraazapentamethine direct dyes that can be used according to the invention, we may mention the cationic dyes described in patent applications WO 95/15144, WO 95/01772 and EP 714954; FR 2189006, FR 2285851, FR-2140205, EP 1378544, EP 1674073.

Thus, quite particularly we may mention the following dyes of formulae (I) to (IV), and preferably the compounds of formulae (I) and (III):

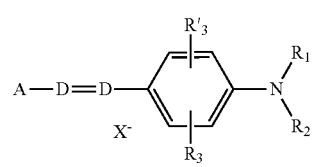

(I)

in which:
D represents a nitrogen atom or the —CH group,
$R_1$ and $R_2$, which may be identical or different, represent a hydrogen atom; a $C_1$-$C_4$ alkyl radical which can be substituted with a —CN, —OH or —$NH_2$ radical or can form, with a carbon atom of the benzene ring, a heterocycle optionally containing oxygen or nitrogen, which can be substituted with one or more $C_1$-$C_4$ alkyl radicals; a 4'-aminophenyl radical,
$R_3$ and $R'_3$, which may be identical or different, represent a hydrogen atom or halogen atom selected from chlorine, bromine, iodine and fluorine, a cyano, $C_1$-$C_4$ alkyl, $C_1$-$C_4$ alkoxy or acetyloxy radical, X⁻ represents an anion preferably selected from chloride, methylsulphate and acetate,
A represents a group selected from the following structures A1 to A18:
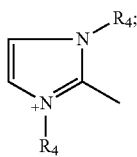   A₁
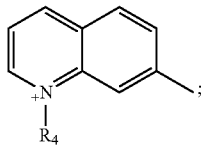   A₂
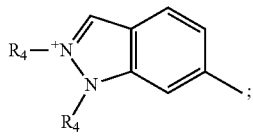   A₃
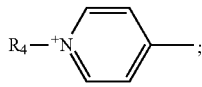   A₄
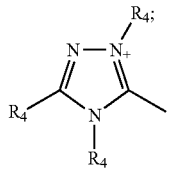   A₅
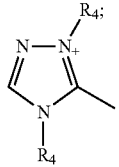   A₆
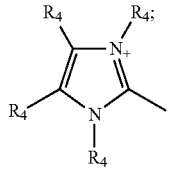   A₇
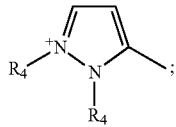   A₈
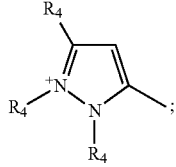   A₉
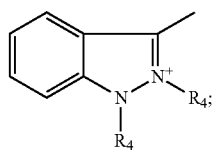   A₁₀
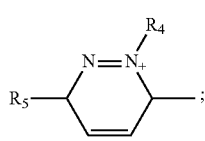   A₁₁
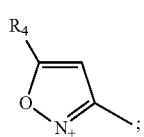   A₁₂
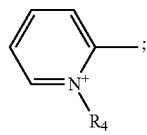   A₁₃
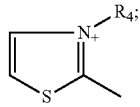   A₁₄
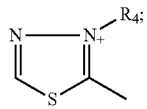   A₁₅
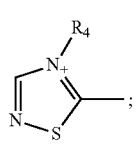   A₁₆
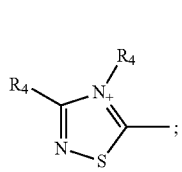   A₁₇
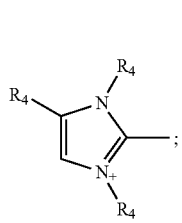   A₁₈
in which $R_4$ represents a $C_1$-$C_4$ alkyl radical which can be substituted with a hydroxyl radical and $R_5$ represents a $C_1$-$C_4$ alkoxy radical;

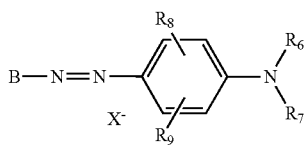

(II)

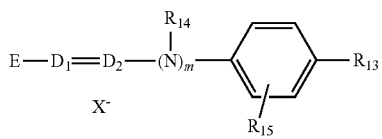

(III)

in which:

$R_6$ represents a hydrogen atom or a $C_1$-$C_4$ alkyl radical, $R_7$ represents a hydrogen atom, an alkyl radical which can be substituted with a —CN radical or with an amino group, a 4'-aminophenyl radical or forms with $R_6$ a heterocycle optionally containing oxygen and/or nitrogen which can be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl radical or $C_1$-$C_4$ alkoxy radical, a —CN radical, $X^-$ represents an anion preferably selected from chloride, methylsulphate and acetate, B represents a group selected from the following structures B1 to B6:

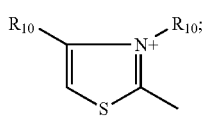

B1

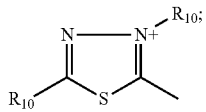

B2

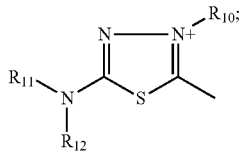

B3

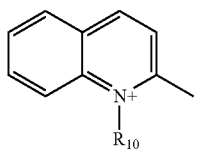

B4

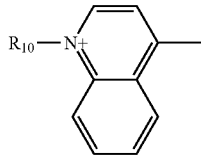

B5

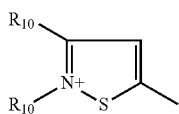

B6 in which $R_{10}$ represents a $C_1$-$C_4$ alkyl radical, $R_{11}$ and $R_{12}$, which may be identical or different, represent a hydrogen atom or a $C_1$-$C_4$ alkyl radical;

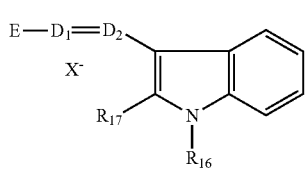

(III')

in which:

$R_{13}$ represents a hydrogen atom, a $C_1$-$C_4$ alkoxy radical, a halogen atom such as bromine, chlorine, iodine or fluorine, $R_{14}$ represents a hydrogen atom, a $C_1$-$C_4$ alkyl radical or forms, with a carbon atom of the benzene ring, a heterocycle optionally containing oxygen and/or substituted with one or more $C_1$-$C_4$ alkyl groups, $R_{15}$ represents a hydrogen atom or a halogen atom such as bromine, chlorine, iodine or fluorine, $R_{16}$ and $R_{17}$, which may be identical or different, represent a hydrogen atom or a $C_1$-$C_4$ alkyl radical, $D_1$ and $D_2$, which may be identical or different, represent a nitrogen atom or the —CH group, m=0 or 1, $X^-$ represents an anion preferably selected from chloride, methylsulphate and acetate, E represents a group selected from the following structures E1 to E8:

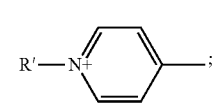

E1

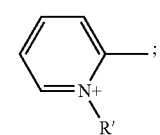

E2

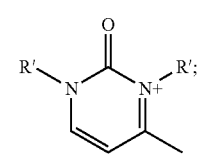

E3

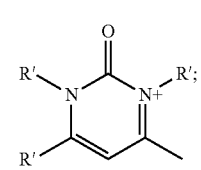

E4

-continued

E5:

[structure: indazole with OH and methyl, N-R', N+-R']

[structure: benzothiazole, N+-R', methyl]

[structure: 3-methylpyridinium, N+-R'] et

[structure: triazole with R' groups and methyl]

in which R' represents a $C_1$-$C_4$ alkyl radical;

when m=0 and $D_1$ represents a nitrogen atom, then E can also denote a group with the following structure E9:

E9

[structure: imidazolium with R' groups and methyl]

in which R' represents a $C_1$-$C_4$ alkyl radical.

$$G-N=N-J \quad (IV)$$

in which:

the symbol G represents a group selected from the following structures $G_1$ to $G_3$:

$G_1$

[structure: pyrazolium with $R_{20}$, $R_{21}$, $R_{19}$, $R_{18}$, methyl, X″]

-continued $G_2$

[structure: 5-membered ring with $R_{20}$, $R_{21}$, Z, N+-$R_{18}$, methyl, X″]

$G_3$

[structure with $R_{23}$, $R_{24}$, K, P, M, methyl]

and in said structures $G_1$ to $G_3$, $R_{18}$ denotes a $C_1$-$C_4$ alkyl radical, a phenyl radical which can be substituted with a $C_1$-$C_4$ alkyl radical or a halogen atom selected from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with one or more $C_1$-$C_4$ alkyl radicals, $C_1$-$C_4$ alkoxy radicals, or $NO_2$, or form together in $G_2$ a benzene ring optionally substituted with one or more $C_1$-$C_4$ alkyl radicals, $C_1$-$C_4$ alkoxy radicals, or $NO_2$;

$R_{20}$ can moreover denote a hydrogen atom;

Z denotes an oxygen atom, a sulphur atom or a group —$NR_{19}$;

M represents a group —CH, —CR (R denoting $C_1$-$C_4$ alkyl), or —$NR_{22}(X^-)_r$;

K represents a group —CH, —CR(R denoting $C_1$-$C_4$ alkyl), or —$NR_{22}(X^-)_r$;

P represents a group —CH, —CR(R denoting $C_1$-$C_4$ alkyl), or —$NR_{22}(X^-)_r$; r denotes zero or 1;

$R_{22}$ represents an atom $O^-$, a $C_1$-$C_4$ alkoxy radical, or a $C_1$-$C_4$ alkyl radical;

$R_{23}$ and $R_{24}$, which may be identical or different, represent a hydrogen atom or a halogen atom selected from chlorine, bromine, iodine and fluorine, a $C_1$-$C_4$ alkyl radical, $C_1$-$C_4$ alkoxy radical, an —$NO_2$ radical;

$X^-$ represents an anion preferably selected from chloride, iodide, methylsulphate, ethylsulphate, acetate and perchlorate;

provided that, if $R_{22}$ denotes $O^-$, then r denotes zero;

if K or P or M denote —N-alkyl $C_1$-$C_4$ $X^-$, then $R_{23}$ or $R_{24}$ may or may not be different from a hydrogen atom;

if K denotes —$NR_{22}(X^-)_r$, then M=P=CH, —CR;

if M denotes —$NR_{22}(X^-)_r$, then K=P=CH, —CR;

if P denotes —$NR_{22}(X^-)_r$, then K=M and they denote —CH or —CR;

if Z denotes a sulphur atom with $R_{21}$ denoting $C_1$-$C_4$ alkyl, then $R_{20}$ is different from a hydrogen atom;

if Z denotes —$NR_{22}$ with $R_{19}$ denoting $C_1$-$C_4$ alkyl, then at least one of the radicals $R_{18}$, $R_{20}$ or $R_{21}$ of the group with structure $G_2$ is different from a $C_1$-$C_4$ alkyl radical;

the symbol J represents:

(a) a group with the following structure $J_1$:

$J_1$

[structure: benzene ring with $R_{27}$, $R_{25}$, $R_{26}$]

and in said structure $J_1$, $R_{25}$ represents a hydrogen atom, a halogen atom selected from chlorine, bromine, iodine and fluorine, a $C_1$-$C_4$ alkyl radical, $C_1$-$C_4$ alkoxy radical, a radical —OH, —$NO_2$, —$NHR_{28}$, —$NR_{29}R_{30}$, —NHCO—$C_1$-$C_4$ alkyl, or forms with $R_{26}$ a ring with 5 or 6 ring members which may or may not contain one or more heteroatoms selected from nitrogen, oxygen or sulphur;

$R_{26}$ represents a hydrogen atom, a halogen atom selected from chlorine, bromine, iodine and fluorine, a $C_1$-$C_4$ alkyl radical, $C_1$-$C_4$ alkoxy radical, or forms with $R_{27}$ or $R_{28}$ a ring with 5 or 6 ring members which may or may not contain one or more heteroatoms selected from nitrogen, oxygen or sulphur;

$R_{27}$ represents a hydrogen atom, a radical —OH, a radical —$NHR_{28}$, a radical

—$NR_{29}R_{30}$;

$R_{28}$ represents a hydrogen atom, a $C_1$-$C_4$ alkyl radical, a $C_1$-$C_4$ monohydroxyalkyl radical, $C_2$-$C_4$ polyhydroxyalkyl radical, a phenyl radical;

$R_{29}$ and $R_{30}$, which may be identical or different, represent a $C_1$-$C_4$ alkyl radical, a $C_1$-$C_4$ monohydroxyalkyl radical, a $C_2$-$C_4$ polyhydroxyalkyl radical;

(b) a nitrogen-containing heterocyclic group with 5 or 6 ring members which can contain other heteroatoms and/or carbonyl-containing groups and which can be substituted with one or more $C_1$-$C_4$ alkyl, amino or phenyl radicals, and notably a group with the following structure $J_2$:

and in said structure $J_2$, $R_{31}$ and $R_{32}$, which may be identical or different, represent a hydrogen atom, a $C_1$-$C_4$ alkyl radical, a phenyl radical;

Y denotes the radical —CO— or the radical n=0 or 1, with, when n denotes 1, U denotes the radical —CO—.

In structures (I) to (IV) defined above, the $C_1$-$C_4$ alkyl or alkoxy group preferably denotes methyl, ethyl, butyl, methoxy, ethoxy.

Among the compounds of formulae (I) and (III), the following compounds are preferred:

We may also mention, among the direct dyes that can be used, the methine dyes such as Basic Red 14, as well as the azo direct dyes notably selected from the following dyes, described in the COLOUR INDEX INTERNATIONAL 3rd edition:
Disperse Red 17
Basic Red 22
Basic Red 76
Basic Yellow 57
Basic Brown 16
Basic Brown 17
Disperse Black 9.

We may also mention 1-(4'-aminodiphenylazo)-2-methyl-4bis-(β-hydroxyethyl)aminobenzene.

Among the quinone direct dyes we may mention the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 as well as the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis-(β,γ-dihydroxypropylamino)-anthraquinone.

Among the azine dyes, we may mention the following compounds:

Basic Blue 17
Basic Red 2.

Among the triarylmethane dyes that can be used according to the invention, we may mention the following compounds:

Basic Green 1
Basic Violet 3
Basic Violet 14
Basic Blue 7
Basic Blue 26

Among the indoamino dyes that can be used according to the invention, we may mention the following compounds:

2-β-Hydroxyethlyamino-5-[bis-(β-4'-hydroxyethyl)amino]anilino-1,4-benzoquinone
2-β-Hydroxyethylamino-5-(2'-methoxy-4'-amino)anilino-1,4-benzoquinone
3-N(2'-Chloro-4'-hydroxy)phenyl-acetylamino-6-methoxy-1,4-benzoquinone imine
3-N(3'-Chloro-4'-methylamino)phenyl-ureido-6-methyl-1,4-benzoquinone imine
3-[4'-N-(Ethyl, carbamylmethyl)-amino]-phenyl-ureido-6-methyl-1,4-benzoquinone imine.

Among the dyes of the tetraazapentamethine type that can be used according to the invention, we may mention the compounds shown in the following table below, An being defined as previously:

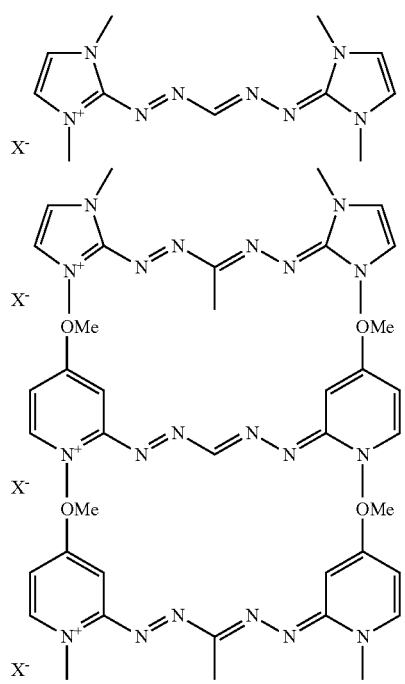

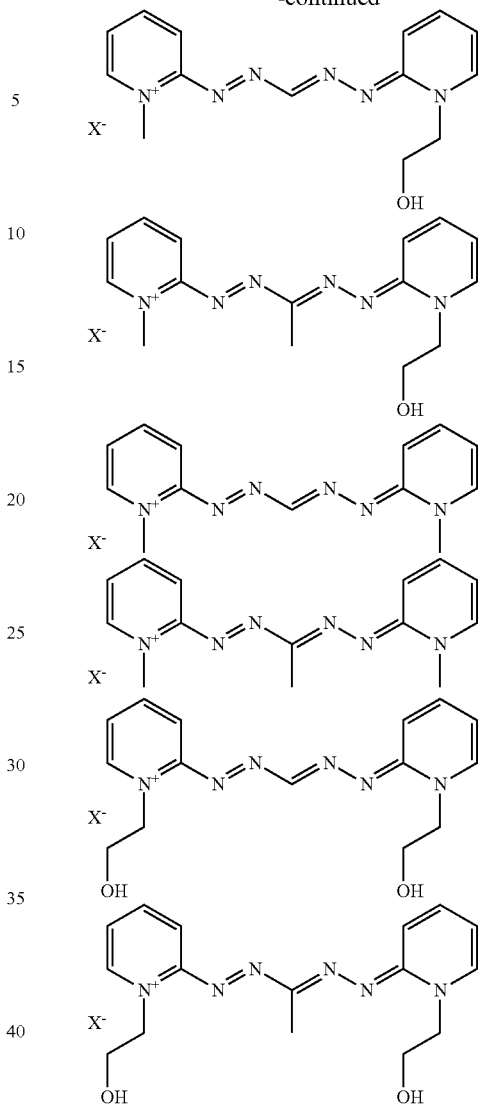

X⁻ represents an anion preferably selected from chloride, iodide, methylsulphate, ethylsulphate, acetate and perchlorate.

Among the polychromophoric dyes, we may mention more particularly the di- or tri-chromophoric azo and/or azomethine (hydrazone) dyes, symmetric or asymmetric, comprising on the one hand at least one aromatic heterocycle containing 5 or 6 ring members, optionally condensed, including at least one quaternized nitrogen atom incorporated in said heterocycle and optionally at least one other heteroatom (such as nitrogen, sulphur, oxygen), and on the other hand, at least one phenyl or naphthyl group, optionally substituted, optionally bearing at least one group OR with R representing a hydrogen atom, a $C_1$-$C_6$ alkyl radical optionally substituted, a phenyl nucleus optionally substituted, or at least one group $N(R')_2$ with R', identical or different, representing a hydrogen atom, a $C_1$-$C_6$ alkyl radical optionally substituted, a phenyl nucleus optionally substituted; the radicals R' can form, with the nitrogen atom to which they are attached, a saturated heterocycle with 5 or 6 ring members, or alternatively the one and/or the two radicals R' can each form with the carbon atom of the aromatic ring positioned ortho to the nitrogen atom, a saturated heterocycle with 5 or 6 ring members.

As cationic aromatic heterocycle, we may preferably mention the rings with 5 or 6 ring members containing 1 to 3 nitrogen atoms, preferably 1 or 2 nitrogen atoms, one being quaternized; said heterocycle moreover being optionally condensed to a benzene nucleus. It should also be noted that the heterocycle can optionally include another heteroatom different from nitrogen, such as sulphur or oxygen.

If the heterocycles or phenyl or naphthyl groups are substituted, they are substituted for example with one or more $C_1$-$C_8$ alkyl radicals optionally substituted with a hydroxyl group, $C_1$-$C_2$ alkoxy, $C_2$-$C_4$ hydroxyalkoxy, acetylamino, amino substituted with one or two $C_1$-$C_4$ alkyl radicals, optionally bearing at least one hydroxyl group or the two radicals which form, with the nitrogen atom to which they are attached, a heterocycle with 5 or 6 ring members, optionally comprising another heteroatom identical or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

These polychromophores are joined together by at least one linkage comprising optionally at least one quaternized nitrogen atom which is or is not incorporated in a saturated or unsaturated, optionally aromatic heterocycle.

Preferably, the linkage is a linear, branched or cyclic $C_1$-$C_{20}$ alkyl chain, optionally interrupted by at least one heteroatom (such as nitrogen, oxygen) and/or by at least one group containing them (CO, $SO_2$), optionally interrupted by at least one condensed or uncondensed heterocycle with a phenyl nucleus and comprising at least one quaternized nitrogen atom incorporated in said ring and optionally at least one other heteroatom (such as oxygen, nitrogen or sulphur), optionally interrupted by at least one substituted or unsubstituted phenyl or naphthyl group, optionally at least one quaternary ammonium group substituted with two $C_1$-$C_{15}$ alkyl groups, optionally substituted; and the linkage does not contain a nitro, nitroso or peroxo group.

The linkage and each chromophore are generally joined together by a heteroatom substituting the phenyl or naphthyl nucleus or by the quaternized nitrogen atom of the cationic heterocycle.

The dye can contain identical or different chromophores.

For examples of such dyes, reference may notably be made to patent applications EP 1637566, EP 1619221, EP 1634926, EP 1619220, EP 1672033, EP 1671954, EP 1671955, EP 1679312, EP 1671951, EP167952, EP167971, WO 06/063866, WO 06/063867, WO 06/063868, WO 06/063869, EP 1408919, EP 1377264, EP 1377262, EP 1377261, EP 1377263, EP 1399425, EP 1399117, EP 1416909, EP 1399116, EP 1671560.

It is also possible to use cationic direct dyes mentioned in applications EP 1006153, which describes dyes having two chromophores of the anthraquinone type joined by a cationic linkage; EP 1433472, EP 1433474, EP 1433471 and EP 1433473 which describe dichromophoric dyes, identical or different, connected by a cationic linkage or otherwise, as well as EP 6291333 which notably describes dyes containing three chromophores, one of them being an anthraquinone chromophore joined to two chromophores of the azo or diazacarbocyanine type or an isomer thereof.

Among the natural direct dyes that can be used according to the invention, we may mention lawsone, juglone, alizarine, purpurin, carminic acid, kermesic acid, purpurogallin, protocatechaldehyde, indigo, isatin, curcumin, spinulosin, apigenidin, the orceins. We can also use extracts or decoctions containing these natural dyes and notably cataplasms or extracts based on henna.

When they are present, the direct dye(s) represent more particularly from 0.0001 to 10 wt. % of the total weight of the composition, and preferably from 0.005 to 5 wt. %.

As stated previously, the composition according to the invention includes one or more fatty esters.

"Fatty esters" means, in the sense of the present invention, more particularly an ester of carboxylic acid comprising in its structure a fatty chain with at least 10 carbon atoms, preferably having from 10 to 30 carbon atoms, preferably from 10 to 22 carbon atoms, and an alcohol which is preferably a monohydric alcohol, notably $C_1$-$C_{30}$, more particularly $C_1$-$C_{22}$, or a sugar.

More particularly, these compounds are selected from:
the esters of saturated linear or branched $C_1$-$C_{30}$ monohydric alcohols, with $C_{10}$-$C_{30}$ monofunctional fatty acids, and the latter can be linear or branched, saturated or unsaturated;
the esters of linear or branched $C_3$-$C_8$ monohydric alcohols, with $C_{10}$-$C_{30}$ bifunctional fatty acids, and the latter can be linear or branched, saturated or unsaturated;
the esters and diesters of sugars and of $C_{10}$-$C_{30}$ fatty acids; mixtures thereof.

With regard to the esters of saturated linear or branched $C_1$-$C_{30}$ monohydric alcohols, with monofunctional $C_{10}$-$C_{30}$ fatty acids, the latter can be linear or branched, saturated or unsaturated. If they are unsaturated, these compounds can contain one to three conjugated or unconjugated carbon-carbon double bonds (—C═C—).

According to a preferred embodiment of the invention, said esters can be selected notably from oleate, laurate, palmitate, myristate, behenate, cocoate, stearate, linoleate, linolenate, caprate, arachidonate, or mixtures thereof, notably such as the oleopalmitates, oleostearates, palmitostearates of $C_1$-$C_{30}$ monohydric alcohols. Among these esters, isopropyl palmitate, isopropyl myristate, octyl dodecyl stearate and isononyl isononaoate are employed more particularly.

Among the esters of linear or branched $C_3$-$C_8$ monohydric alcohols, with bifunctional, linear or branched, saturated or unsaturated $C_{12}$-$C_{30}$ fatty acids, and more particularly among the isopropyl diester of sebacic acid, also called diisopropyl sebacate, The composition can also include, as fatty ester, the esters and diesters of sugars and $C_{10}$-$C_{30}$ fatty acids. As a reminder, "sugar" means compounds that possess several alcohol functions, with or without an aldehyde or ketone function, and that have at least 4 carbon atoms. Said sugars can be monosaccharides, oligosaccharides or polysaccharides.

As suitable sugars, we may mention for example sucrose, glucose, galactose, ribose, fucose, maltose, fructose, mannose, arabinose, xylose, lactose, and their derivatives, notably alkylated, such as methylated derivatives, for instance methylglucose.

The esters of sugars and of fatty acids can notably be selected from the group comprising the esters or mixtures of esters of sugars described previously and of linear or branched, saturated or unsaturated $C_{10}$-$C_{22}$ fatty acids. If they are unsaturated, these compounds can contain one to three conjugated or unconjugated carbon-carbon double bonds.

The esters can also be selected from mono-, di-, tri- and tetra-esters, polyesters and mixtures thereof.

These esters can be for example oleates, laurates, palmitates, myristates, behenates, cocoates, stearates, linoleates, linolenates, caprates, arachidonates of sugar(s), or mixtures thereof, such as notably the oleopalmitate, oleostearate, palmitostearate mixed esters of sugar(s).

More particularly, the mono- and di-esters are used, and notably mono- or di-oleate, stearate, behenate, oleopalmitate, linoleate, linolenate, oleostearate, of sucrose, of glucose or of methylglucose.

We may mention as an example the product sold under the designation Glucate® DO by the company Amerchol, which is a methylglucose dioleate.

We may also mention as examples of esters or of mixtures of esters of sugar of fatty acid:
- the products sold under the designations F160, F140, F110, F90, F70, SL40 by the company Crodesta, denoting respectively the palmitostearates of sucrose formed from 73% of monoester and 27% of di- and tri-ester, from 61% of monoester and 39% of di-, tri- and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and sucrose monolaurate;
- the products sold under the designation Ryoto Sugar Esters for example under reference B370 and corresponding to sucrose behenate formed from 20% of monoester and 80% of di-triester-polyester;
- the sucrose mono-di-palmitostearate marketed by the company Goldschmidt under the designation Tegosoft® PSE.

Compounds selected from the esters of saturated, linear or branched $C_1$-$C_{18}$ monohydric alcohols, with monofunctional $C_{14}$-$C_{18}$ fatty acids, the latter being linear or branched, saturated or unsaturated, are preferably used as fatty ester.

The composition according to the invention has a content of fatty ester(s) advantageously between 0.3 and 12.5 wt. %, relative to the weight of the composition, preferably between 0.5 and 10 wt. % and according to an even more preferred variant of the invention, from 0.6 to 9 wt. %.

The composition according to the invention additionally includes one or more fatty alcohols.

More particularly, said fatty alcohol is selected from the non-(poly)oxyalkylenated (the alkyl having 1 to 3 carbon atoms) and non-(poly)glycerolated alcohols, comprising one or more fatty chains having from 10 to 30 carbon atoms, more particularly from 14 to 22 carbon atoms and even more advantageously, from 16 to 18 carbon atoms, saturated or unsaturated, the fatty chains being optionally substituted with one or two additional hydroxyl groups. When the alcohol is unsaturated, it has from 1 to 3 conjugated or unconjugated carbon-carbon double bonds (—C═C—). Preferably, the fatty alcohol is a monohydric alcohol.

As examples of fatty alcohols, we may mention lauryl, cetyl, stearyl, behenyl, myristyl, linoleyl, undecylenyl, palmitoleyl, linolenyl, arachidonyl, erucyl, isocetyl, isostearyl, isobehenyl alcohol, oleyl alcohol and mixtures thereof.

Preferably, the composition includes one or more non-(poly)oxyalkylenated and non-(poly)glycerolated monohydric fatty alcohols, having from 14 to 22 carbon atoms and more specifically from 16 to 18 carbon atoms, saturated.

According to one embodiment of the invention, the composition has a content of fatty alcohol(s) between 3 and 25 wt. %, relative to the weight of the composition, preferably between 5 and 20 wt. % and according to a more preferred variant of the invention, from 6 to 18 wt. %.

It should be noted that according to a very advantageous characteristic of the invention, the fatty ester or esters and the fatty alcohol or alcohols are present in amounts such that the weight ratio of fatty alcohol(s) to fatty ester(s) is greater than 2 and less than 10. Preferably, the weight ratio of fatty alcohol(s) to fatty ester(s) is between 3 and 9.

The composition according to the invention further includes one or more cationic surfactants.

More particularly, said surfactants are selected from the compounds having one or more cationic charges and one or more $C_{12}$-$C_{30}$ alkyl or alkenyl chains, optionally bearing one or more ester or amide functions. It is further specified that the cationic surfactants included in the composition according to the invention do not carry an anionic charge. Therefore these surfactants are not amphoteric or zwitterionic species.

As examples of suitable cationic surfactants, we may mention:
(i) quaternary ammonium salts of the following formula (V):

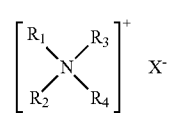

in which
X⁻ is an anion selected for example from the halides (chloride, bromide or iodide) or alkyl($C_2$-$C_6$)sulphates more particularly methylsulphate, the phosphates, the alkyl- or alkarylsulphonates, anions derived from organic acid such as acetate or lactate, and
(1) the radicals $R_1$ to $R_3$, which may be identical or different, represent an aliphatic radical, more particularly linear or branched, $C_1$-$C_4$ alkyl, or an aryl or alkaryl radical, the alkyl radical optionally bearing an alkoxy group, alkyl amide,
$R_4$ denotes a linear or branched, $C_{16}$-$C_{30}$, preferably $C_{18}$-$C_{22}$ alkyl radical; or
(2) the radicals $R_1$ and $R_2$, which may be identical or different, represent an aliphatic radical, more particularly linear or branched, $C_1$-$C_4$ alkyl, or an aryl or alkaryl radical, the alkyl radical optionally bearing an alkoxy group, alkyl amide or $C_1$-$C_4$ hydroxyalkyl;
$R_3$ and $R_4$, which may be identical or different, denote a linear or branched, $C_{12}$-$C_{30}$ alkyl or alkenyl radical, said radical optionally having at least one ester or amide function;
Advantageously, the cationic surfactant according to the aforementioned option (1) is a behenyl trimethyl ammonium salt (for example chloride), and according to option (2) a stearamidopropyl dimethyl (myristylacetate) ammonium salt (for example chloride) marketed under the designation "CERAPHYL 70" by the company VAN DYK.
(ii) the quaternary ammonium salts of imidazolinium of the following formula (VI):

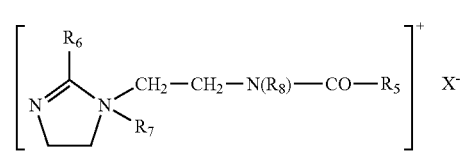

in which $R_5$ represents a $C_{12}$-$C_{30}$ alkenyl or alkyl radical, $R_6$ represents a hydrogen atom, a $C_1$-$C_4$ alkyl radical or a $C_{12}$-$C_{30}$ alkenyl or alkyl radical, $R_7$ represents a $C_1$-$C_4$ alkyl radical, $R_8$ represents a hydrogen atom, a $C_1$-$C_4$ alkyl radical, X is an anion, X notably being selected from the halides, phosphates, acetates, lactates, alkyl sulphates, alkyl or alkaryl sulphonates.

Preferably, $R_5$ and $R_6$ denote a mixture of alkenyl or alkyl radicals having from 12 to 21 carbon atoms, for example derived from tallow fatty acids, $R_7$ denotes methyl, $R_8$ denotes hydrogen. Such a product is for example Quaternium-27 (CTFA 1997) or Quaternium-83 (CTFA 1997) marketed under the designations "REWOQUAT" W 75, W90, W75PG, W75HPG by the company WITCO;

(iii) the quaternary diammonium salts of formula (VII):

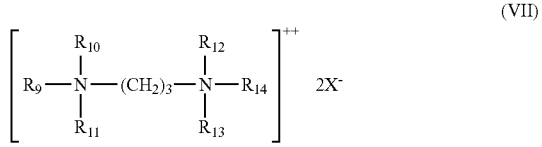

(VII)

in which $R_9$ denotes a $C_{12}$-$C_{30}$ alkyl or alkenyl radical, $R_{10}$, $R_{11}$, $R_{12}$, $R_{13}$ and $R_{14}$, which may be identical or different, are selected from hydrogen or a $C_1$-$C_4$ alkyl radical, and X is an anion notably selected from the halides, acetates, phosphates, nitrates and methyl sulphates.

Said quaternary diammonium salts notably include propanetallow diammonium dichloride.

(iv) the quaternary ammonium salts containing at least one ester function of the following formula (VIII):

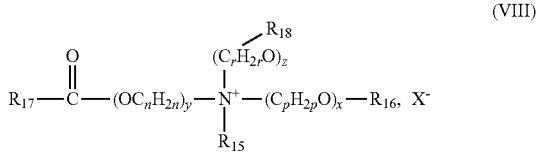

(VIII)

in which:

$R_{15}$ is selected from the $C_1$-$C_6$ alkyl, $C_1$-$C_6$ hydroxyalkyl, $C_2$-$C_6$ dihydroxyalkyl radicals;

$R_{16}$ is selected from the $R_{19}$—CO— radical, an $R_{20}$ $C_1$-$C_{22}$ linear or branched alkyl or alkenyl radical, a hydrogen atom, $R_{18}$ is selected from the radical $R_{21}$—CO—, an $R_{22}$ alkyl or alkenyl $C_1$-$C_6$ linear or branched radical, a hydrogen atom, $R_{17}$, $R_{19}$ and $R_{21}$, which may be identical or different, are selected from the linear or branched $C_{12}$-$C_{22}$ alkyl or alkenyl radicals;

n, p and r, which may be identical or different, are integers with a value from 2 to 6;

y is an integer with a value from 1 to 10;

x and z, which may be identical or different, are integers with a value from 0 to 10;

$X^-$ is a simple or complex, organic or inorganic anion.

More particularly the ammonium salts of formula (VIII) are used in which:

$R_{15}$ denotes a methyl or ethyl radical, x and y are equal to 1;

z is equal to 0 or 1;

n, p and r are equal to 2;

$R_{16}$ is selected from the radical $R_{19}$—CO—, methyl, ethyl, $C_{14}$-$C_{22}$ alkyl or alkenyl radicals; a hydrogen atom;

$R_{17}$, $R_{19}$ and $R_{21}$, which may be identical or different, are selected from the $C_7$-$C_{21}$, linear or branched, saturated or unsaturated alkyl or alkenyl radicals;

$R_{18}$ is selected from the radical $R_{21}$—CO—, a hydrogen atom.

Such compounds are for example marketed under the designations DEHYQUART by the company COGNIS, STEPANQUAT by the company STEPAN, NOXAMIUM by the company CECA, REWOQUAT WE 18 by the company REWO-WITCO.

(v) or mixtures thereof.

According to a particularly advantageous embodiment of the invention, the composition includes, as cationic surfactant, one or more cationic surfactants of formula (V), and preferably one or more cationic surfactants of formula (V) corresponding to option (1).

According to one embodiment of the invention, the composition has a content of cationic surfactant(s) between 0.01 and 25 wt. %, relative to the weight of the composition, preferably between 0.05 and 20 wt. % and according to a variant particular of the invention, from 0.1 to 18 wt. %.

According to a preferred characteristic of the invention, the cationic surfactant and the fatty alcohol are present in amounts such that the weight ratio of fatty alcohol(s) to cationic surfactant(s) is greater than or equal to 1, more particularly greater than or equal to 2. Preferably, said weight ratio is between 1 and 50, more advantageously between 2 and 30.

The cosmetically acceptable medium generally comprises water or a mixture of water and one or more organic solvents.

As organic solvent, we may mention for example the linear or branched, $C_2$-$C_4$ alkanols, such as ethanol and isopropanol; the polyols and ethers of polyols such as 2-butoxyethanol, propylene glycol, dipropylene glycol, propylene glycol monomethyl ether, monoethyl ether and monomethyl ether of diethylene glycol, glycerol as well as aromatic alcohols such as benzyl alcohol or phenoxyethanol, and mixtures thereof.

The solvent or solvents can be present in proportions preferably in the range from 1 to 40 wt. % relative to the total weight of the dyeing composition, and even more preferably from 5 to 30 wt. %.

The compositions according to the invention can also include various additives used conventionally in the field of the colouring of human keratin fibres.

The composition can thus include inorganic or organic thickeners, and in particular non-ionic, anionic, cationic or amphoteric polymers, optionally associative; dulling or opacifying agents such as titanium oxides; anionic, nonionic, amphoteric or zwitterionic surfactants; penetrants, sequestering agents, such as ethylenediamine tetraacetic [acid] or salts thereof; dispersants; film-forming agents; preservatives; vitamins; perfumes; ceramides; volatile or non-volatile non-cationic silicones; UV filters; vegetable or mineral oils.

The additives as defined above can be present in an amount for each of them between 0.01 and 40 wt. %, preferably between 0.1 and 30 wt. % relative to the total weight of the composition.

The composition can also contain one or more antioxidants such as ascorbic acid, erythorbic acid. It can also include one or more reducing agents such as ammonium sulphite, bisulphite or metabisulphite or ammonium thiolactate.

Usually, the contents of reducing agents and antioxidants, when present, vary from 0.005 to 12 wt. % relative to the total weight of the composition, preferably from 0.1 to 8 wt. %.

The composition according to the invention can also optionally include one or more cationic or amphoteric substantive polymers.

The substantive character (i.e. the capacity for deposition on the hair) of the polymers is determined conventionally using the test described by Richard J. Crawford, Journal of the Company of Cosmetic Chemists, 1980, 31-(5)-pages 273 to 278 (detection by Red 80 acid dye).

These substantive polymers are notably described in patent application EP 557203.

More particularly, we can employ polymers selected from cationic cellulose derivatives, homopolymers of dimethyldiallylammonium halide (for example Merquat 100) and copolymers of dimethyldiallylammonium halide and of (meth)acrylic acid; homopolymers and copolymers of methacryloyloxyethyl-trimethylammonium halide; quaternary polyammonium polymers; vinylpyrrolidone polymers with cationic units; and mixtures thereof.

Among the substantive polymers of the dimethyldiallylammonium halide copolymer type that can be used according to the invention, we may mention in particular:

the copolymers of diallyldimethylammonium chloride and acrylic acid such as that with proportions (80/20 by weight) sold under the designation Merquat 280 by the company Calgon;

the copolymers of dimethyldiallylammonium chloride and acrylamide sold under the designations Merquat 550 and Merquat S by the company Merck.

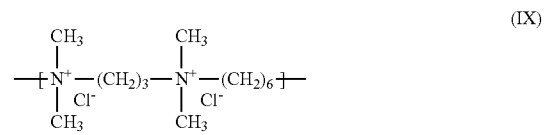

notably those whose molecular weight, determined by gel permeation chromatography, is between 9500 and 9900;

the polymers prepared and described in French patent 2 270 846, constituted of repeating units corresponding to the following formula (X):

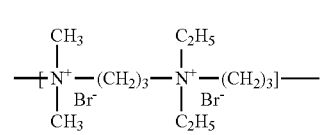

notably those whose molecular weight, determined by gel permeation chromatography, is about 1200;

the polymers described and prepared in U.S. Pat. Nos. 4,157,388, 4,390,689, 4,702,906, 4,719,282, and constituted of repeating units corresponding to the following formula (XI):

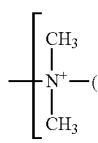

Among the substantive polymers of the methacryloyloxyethyltrimethylammonium halide polymer type that can be used according to the invention, we may mention in particular the products that are designated in the CTFA dictionary (5th edition, 1993) "Polyquaternium 37", "Polyquaternium 32" and "Polyquaternium 35", which correspond respectively, with respect to "Polyquaternium 37", to crosslinked poly(methacryloyloxyethyltrimethyl-ammonium chloride), in dispersion at 50% in mineral oil, and sold under the designation Salcare SC95 by the company Allied Colloids; with respect to "Polyquaternium 32", to the crosslinked copolymer of acrylamide and methacryloyloxyethyltrimethylammonium chloride (20/80 by weight), in dispersion at 50% in mineral oil, and sold under the designation Salcare SC92 by the company Allied Colloids; and with respect to "Polyquaternium 35", to the methosulphate of the methacryloyloxyethyltrimethylammonium/methacryloyloxyethyldimethylacetylammonium copolymer, sold under the designation Plex 7525L by the company Rohm GmbH.

The substantive polymers of the quaternary polyammonium type that can be used according to the invention are as follows:

the polymers prepared and described in French patent 2 270 846, constituted of repeating units corresponding to the following formula (IX):

in which p denotes an integer from 1 to about 6, D can be zero or can represent a group —(CH$_2$)$_r$—CO— in which r denotes a number equal to 4 or 7, and notably those whose molecular weight is less than 100 000, preferably less than or equal to 50 000; such polymers are notably sold by the company Miranol under the designations "Mirapol A15", "Mirapol AD1", "Mirapol AZ1" and "Mirapol 175".

Among the vinyl pyrrolidone polymers (polyvinyl pyrrolidone, PVP) with cationic units for use according to the invention, we may mention in particular:

a) the vinyl pyrrolidone polymers containing dimethylaminoethyl methacrylate units; among these, we may mention:

the vinyl pyrrolidone/dimethylaminoethyl methacrylate copolymer (20/80 by weight) sold under the trade name COPOLYMER 845 by the company I.S.P.

the vinyl pyrrolidone/dimethylaminoethyl methacrylate copolymers quaternized by diethyl sulphate, sold under the designations GAFQUAT 734, 755, 755 S and 755 L by the company I.S.P.

the hydrophilic PVP/dimethylaminoethyl methacrylate/polyurethanes, sold under the trade name PECOGEL GC-310 by the company U.C.I.B., or under the designations AQUAMERE C 1031 and C 1511 by the company BLAGDEN CHEMICALS, the PVP/dimethylaminoethyl methacrylate/C8 to C16 olefins, quaternized or unquaternized, sold under the designations GANEX ACP 1050 to 1057, 1062 to 1069, 1079 to 1086, by the company I.S.P.

the PVP/dimethylaminoethyl methacrylate/vinylcaprolactam, sold under the designation GAFFIX VC 713 by the company I.S.P.

b) the vinyl pyrrolidone polymers containing methacrylamidopropyltrimethylammonium units (M.A.P.T.A.C.), among which we may notably mention:

the vinyl pyrrolidone/M.A.P.T.A.C. copolymers, sold under the trade names GAFQUAT ACP 1011 and GAFQUAT HS 100 by the company I.S.P.

c) the vinyl pyrrolidone polymers containing methylvinylimidazolium units, among which we may mention more particularly:

the PVP/methylvinylimidazolium chlorides, sold under the designations LUVIQUAT FC 370, FC 550, FC 905, HM 552 by the company B.A.S.F.

PVP/methylvinylimidazolium chloride/vinylimidazole, sold under the designation LUVIQUAT 8155 by the company B.A.S.F.

PVP/methylvinylimidazolium methosulphate, sold under the designation LUVIQUAT MS 370 by the company B.A.S.F.

Among the cationic polysiloxanes, we may notably mention those described in patent application EP-A-0557203, from page 8 line 48 to page 11 line 9, and even more particularly the products containing amodimethicone (CTFA designation) of the following formula (XII):

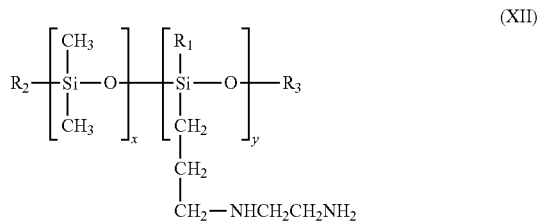

(XII)

in which $R_1$, $R_2$, $R_3$, independently of one another, represent a hydrogen atom, a hydroxyl radical, a $C_1$-$C_4$ alkyl radical, a $C_1$-$C_4$ alkoxy radical; x and y depend on the molecular weight of the compound and its degree of substitution with amine groups.

When they are present, the concentration of cationic or amphoteric substantive polymers can vary between approx. 0.01 and 10 wt. % relative to the weight of the composition, and preferably between 0.1 and 5 wt. % relative to the weight of the composition.

The pH of compositions (A) and (B) according to the invention is greater than 8, generally between 8 and 12 exclusive, and preferably between 9 and 11 exclusive. It can be adjusted to the desired value by means of one or more acidifying agents or one or more alkalizing agents usually employed in this field.

Among the acidifying agents, we may mention for example the organic or inorganic acids such as hydrochloric acid, orthophosphoric acid, sulphuric acid, carboxylic acids such as acetic acid, tartaric acid, citric acid, lactic acid, sulphonic acids.

Among the alkalizing agents we may mention, as examples, ammonia, alkali carbonates, alkanolamines such as the mono-, di- and triethanolamines as well as their derivatives, sodium or potassium hydroxides and compounds of the following formula:

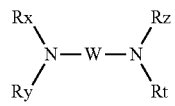

in which W is a propylene residue optionally substituted with a hydroxyl group or a $C_1$-$C_6$ alkyl radical; Rx, Ry, Rz and Rt, which may be identical or different, represent a hydrogen atom, a $C_1$-$C_6$ alkyl or $C_1$-$C_6$ hydroxyalkyl radical.

Preferably, the alkalizing agent is ammonia, optionally combined with one or more other alkalizing agents.

Composition (A) according to the invention can also include one or more oxidizing agents. In this case it is called a ready-to-use composition (B).

In particular, the ready-to-use composition (B) is obtained by extemporaneous mixing, before application, of a dyeing composition (A) previously described, with at least one composition containing one or more oxidizing agents.

The oxidizing agent is preferably selected from hydrogen peroxide, urea peroxide, bromates or ferricyanides of alkali metals, per-acid salts for example persulphates, perborates and percarbonates of alkali or alkaline-earth metals, such as sodium, potassium, magnesium.

Use of hydrogen peroxide is particularly preferred.

Said oxidizing agent is advantageously constituted of hydrogen peroxide in aqueous solution ("hydrogen peroxide") the strength of which can vary, more especially, from 1 to 40 volumes, and even more preferably from 5 to 40 volumes.

According to a first variant, the method according to the invention consists of applying on human keratin fibres, which can be dry or damp, the ready-to-use composition (B) that has just been described, which is obtained by extemporaneous mixing, before application, of a dyeing composition without oxidizing agent (A) with an oxidizing composition.

Said oxidizing composition, whose cosmetically acceptable medium includes at least water, also includes one or more oxidizing agents as defined above.

Regarding the organic solvents optionally present in the oxidizing composition, we may refer to the list given previously when describing the dyeing composition.

Usually, the pH of the oxidizing composition is less than 7.

The oxidizing composition can be in the form of a solution, an emulsion or a gel.

It can optionally include one or more additives used conventionally in the field of the colouring of human keratin fibres, depending on the desired galenical form. Once again, reference may be made to the list of additives given above.

Generally, the degree of dilution of the dyeing composition is such that the resultant composition can easily be applied on the keratin fibres that are to be coloured, while remaining localized in the place where it was applied, thus avoiding problems caused by running of the composition beyond the area to be treated.

More particularly, the degree of dilution (dyeing composition/oxidizing composition) varies from 0.8 to 3, and preferably from 1 to 2.

According to a second variant of the invention, the method according to the invention consists of applying composition (A) without oxidizing agent, and an oxidizing composition successively, without intermediate rinsing.

The oxidizing composition can be applied and then the dyeing composition, or vice versa.

According to a more particular embodiment of this variant, the oxidizing composition is applied on human keratin fibres, dry or damp, before the dyeing composition (A) without oxidizing agent.

According to this option, the conditions are such that following application of the two compositions, the pH of the mixture on the fibres is greater than or equal to 8, more particularly between 8 and 12 and preferably between 8 and 11.

Regardless of the variant adopted, the mixture on the fibres is left in place for a length of time generally of the order of 1 minute to 1 hour, preferably from 10 minutes to 30 minutes.

The temperature during the process is conventionally between room temperature (from 15 to 25° C.) and 80° C., preferably between room temperature and 60° C.

At the end of the treatment, the human keratin fibres are optionally rinsed with water, washed with shampoo, rinsed again with water then dried or left to dry.

The following examples serve to illustrate the invention though without having any limiting character.

EXAMPLE 1

The following composition (1a) is prepared:

TABLE 1a

| Ingredients | Concentration (in g % Active Substance) |
|---|---|
| Cetyl alcohol | 6.25 |
| Stearyl alcohol | 6.25 |
| Stearyl palmitate | 0.75 |
| Stearyl stearate | 1.17 |
| Behentrimonium chloride | 2.97 |
| Paraphenylenediamine | 0.63 |
| Resorcinol | 0.196 |
| 2,4-Diaminophenoxyethanol | 0.98 |
| Erythorbic acid | 0.25 |
| Sodium metabisulphite | 0.45 |
| Ammonia | 4.11 |
| Pentasodium pentetate | 0.08 |
| Water | qs 100 |

The composition thus obtained gives rise to a smooth creamy formula of a white colour.

It is then mixed with an oxidizing composition at 20 volumes of hydrogen peroxide with a weight ratio of composition to oxidizing composition of 1/1.5 then applied on a lock of hair 90% natural white for 30 minutes at room temperature (about 20° C.)

At the end of the pause, the lock of hair is rinsed with water and then dried.

The dyeing power of composition (1a) is compared with that obtained when the following composition (1b) is used in the same conditions:

TABLE 1b

| Ingredients | Concentration (in g % Active Substance) |
|---|---|
| oleyl alcohol polyglycerolated with 2 mol of glycerol | 4 |
| oleyl alcohol polyglycerolated with 4 mol of glycerol | 5.69 |
| oleic acid | 3 |
| oleic amine (2OE) | 7 |
| diethylaminopropyl laurylaminosuccinamate | 3 |
| oleyl alcohol | 5 |
| diethanolamine of oleic acid | 12 |
| propylene glycol | 3.5 |
| ethanol | 7 |
| dipropylene glycol | 0.5 |
| monomethyl ether of propylene glycol | 9 |
| ammonium acetate | 0.8 |
| paraphenylenediamine | 0.63 |
| resorcinol | 0.196 |
| 2,4-diaminophenoxyethanol | 0.98 |
| erythorbic acid | 0.25 |
| sodium metabisulphite | 0.45 |
| EDTA | 0.2 |
| ammonia | 4.11 |
| water | qs 100 |

The coloration is measured using a Minolta CM2600d colorimeter in the CIE Lab system (illuminant D65, angle 10°, specular component included).

The results are shown in the following table:

| Composition | Colour | L* |
|---|---|---|
| composition (1a) | Blue-black | 16.27 |
| composition (1b) | Blue-black | 18.59 |

It is found that the coloration obtained using composition (1a) according to the invention is more intense than that obtained using composition (1b).

Moreover, the coloration of the composition according to the invention (1a) after mixing with the oxidizing agent, develops very selectively on the fibre and very slightly, or not at all, in the composition that remains on the hair as well as in the rinsing water of the lock of hair.

In contrast, the coloration of composition (1b) obtained after mixing with the oxidizing agent increases very strongly, and the coloration is found in the colouring fluid.

Finally, release of ammonia from the composition according to the invention (composition 1a) is always less than that of the reference composition (composition 1b) as can be seen from Table 1c below.

Moreover, the level of release of ammonia for 10 pairs of compositions (1a) and (1b) was evaluated by 3 people immediately after mixing with the oxidizing agent (t=0) and after 15 minutes (t=15 min), on the one hand in the mixing bowl, and on the other hand after applying each composition on the head.

After evaluation, it appears that all the evaluators found considerably less release of ammonia with the ready-to-use compositions of the invention both in the bowl containing the mixtures at t=0 and at t=15 minutes and on the head at t=0 and at t=15 minutes.

EXAMPLE 2

The procedure is the same as for Example 1, comparing the dyeing properties of the following compositions (2a) and (2b):

TABLE 2a

| Ingredients | Concentration (in g % Active Substance) |
|---|---|
| cetyl alcohol | 8.12 |
| stearyl alcohol | 8.12 |
| stearyl palmitate | 0.97 |
| stearyl stearate | 1.53 |
| behentrimonium chloride | 3.89 |
| toluene-2,5-diamine | 0.61 |
| 2,4-diaminophenoxyethanol | 0.01 |
| 6-hydroxyindole | 0.04 |
| p-methylaminophenol sulphate | 0.15 |
| 2-amino-3-hydroxypyridine | 0.02 |
| resorcinol | 0.7 |
| m-aminophenol | 0.165 |
| p-aminophenol | 0.45 |
| erythorbic acid | 0.25 |
| sodium metabisulphite | 0.45 |
| ammonia | 4.94 |
| pentasodium pentetate | 0.08 |
| water | qs 100 |

TABLE 2b

| Ingredients | Concentration (in g % Active Substance) |
|---|---|
| oleyl alcohol polyglycerolated with 2 mol of glycerol | 4 |
| oleyl alcohol polyglycerolated with 4 mol of glycerol | 5.69 |
| oleic acid | 3 |
| oleic amine (2OE) | 7 |
| diethylaminopropyl laurylaminosuccinamate | 3 |
| oleyl alcohol | 5 |
| diethanolamide of oleic acid | 12 |
| propylene glycol | 3.5 |
| ethanol | 7 |
| dipropylene glycol | 0.5 |
| monomethyl ether of propylene glycol | 9 |
| ammonium acetate | 0.8 |
| toluene-2,5-diamine | 0.61 |
| 2,4-diaminophenoxyethanol | 0.01 |
| 6-hydroxyindole | 0.04 |
| p-methylaminophenol sulphate | 0.15 |
| 2-amino-3-hydroxypyridine | 0.02 |
| resorcinol | 0.7 |
| m-aminophenol | 0.165 |
| p-aminophenol | 0.45 |
| erythorbic acid | 0.25 |
| sodium metabisulphite | 0.45 |
| EDTA | 0.2 |
| ammonia | 4.11 |
| water | qs 100 |

The results are presented in the following table:

TABLE 2c

| Composition | Colour | L* |
|---|---|---|
| composition (2a) | Deep golden-blond | 23.14 |
| composition (2b) | Deep golden-blond | 26.14 |

It is found that the coloration obtained using composition (2a) according to the invention is more intense than that obtained using composition (2b).

Moreover, the coloration of the composition according to the invention (2a) after mixing with the oxidizing agent, develops very selectively on the fibre and very slightly, or not at all, in the composition that remains on the hair as well as in the rinsing water of the lock of hair.

In contrast, the coloration of composition (2b) obtained after mixing with the oxidizing agent increases very strongly, and the coloration is also found in the rinsing water.

Finally, it is found that the release of ammonia from the composition according to the invention obtained from composition (2a) is less than from the composition obtained from the reference composition (2b).

EXAMPLE 3

The procedure of Example 1 is followed, and the dyeing properties of the following compositions (3a) and (3b) are compared:

TABLE 3a

| Ingredients | Concentration (in g % Active Substance) |
|---|---|
| cetyl alcohol | 9.37 |
| stearyl alcohol | 9.37 |
| stearyl palmitate | 1.12 |
| stearyl stearate | 1.76 |
| behentrimonium chloride | 4.46 |
| toluene-2,5-diamine | 0.026 |
| 2,4-diaminophenoxyethanol | 0.008 |
| resorcinol | 0.1 |
| m-aminophenol | 0.02 |
| p-aminophenol | 0.039 |
| erythorbic acid | 0.25 |
| sodium metabisulphite | 0.45 |
| ammonia | 5.76 |
| pentasodium pentetate | 0.08 |
| water | qs 100 |

TABLE 3b

| Ingredients | Concentration (in g % Active Substance) |
|---|---|
| oleyl alcohol polyglycerolated with 2 mol of glycerol | 4 |
| oleyl alcohol polyglycerolated with 4 mol of glycerol | 5.69 |
| oleic acid | 3 |
| amine oleic (2OE) | 7 |
| diethylaminopropyl laurylaminosuccinamate | 3 |
| oleyl alcohol | 5 |
| diethanolamide of oleic acid | 12 |
| propylene glycol | 3.5 |
| ethanol | 7 |
| dipropylene glycol | 0.5 |
| monomethyl ether of propylene glycol | 9 |
| ammonium acetate | 0.8 |
| toluene-2,5-diamine | 0.026 |
| 2,4-diaminophenoxyethanol | 0.008 |
| resorcinol | 0.1 |
| m-aminophenol | 0.02 |
| p-aminophenol | 0.039 |
| erythorbic acid | 0.25 |
| sodium metabisulphite | 0.45 |
| EDTA | 0.2 |

TABLE 3b-continued

| Ingredients | Concentration (in g % Active Substance) |
|---|---|
| ammonia solution at 20% ammonia | 5.76 |
| water | qs 100 |

The results are shown in the following table:

TABLE 3c

| Composition | Colour | L* |
|---|---|---|
| composition (3a) | Very light blond with ash-golden sheen | 50.42 |
| composition (3b) | Very light blond with ash-golden sheen | 52.75 |

It is found that the coloration obtained using composition (3a) according to the invention is more intense than that obtained using composition (3b).

Moreover, the coloration of the composition according to the invention (3a) after mixing with the oxidizing agent, develops very selectively on the fibre and very slightly, or not at all, in the composition that remains on the hair as well as in the rinsing water of the lock of hair, whereas this is not the case with composition (3b).

Finally, it is found that the release of ammonia from the composition according to the invention obtained from composition (3a) is less than from the composition obtained from the reference composition (3b).

EXAMPLE 4

The following compositions are prepared (the amounts are expressed in grams-%):

| | Comparative composition | Composition according to the invention |
|---|---|---|
| Glycerine | 5 | 5 |
| EDTA | 0.3 | 0.3 |
| Ascorbic acid | 0.1 | 0.1 |
| Sodium sulphite | 0.3 | 0.3 |
| Ammonia at 20% | 7 | 7 |
| Myristyl alcohol | 0.9 | 1.8 |
| Cetyl alcohol | 6.6 | 13.2 |
| Castor oil | 0.7 | 0.7 |
| Glyceryl stearate | 1.2 | 1 |
| Lauryl alcohol 23 OE | 0.3 | 0.3 |
| Cetylstearyl alcohol 33 OE | 0.9 | 0.9 |
| Stearyltrimethyl ammonium chloride | 3.6 | 3.6 |
| Isopropyl palmitate | 2.6 | 2 |
| Titanium oxide | 0.13 | 0.13 |
| Para-toluenediamine sulphate | 0.63 | 0.63 |
| Resorcinol | 0.98 | 0.98 |
| 2,4-Diaminophenoxyethanol | 0.196 | 0.196 |
| Water | q.s. 100 | q.s. 100 |
| pH | 10.1 | 10.1 |
| Weight ratio fatty alcohol/fatty acid ester | 1.97 | 5.00 |
| Weight ratio fatty alcohol/cationic surfactant | 2.08 | 4.17 |

Each composition is mixed with an identical volume of an oxidizing composition with 20 volumes of hydrogen peroxide.

Two types of measurements were then carried out for each of the mixtures:

1) A colorimeter was used for measuring the variation of the colour of each of the mixtures during a pause of 30 minutes, every 5 minutes, by placing one portion of each mixture in a cell affixed to the reading cell of the colorimeter, avoiding any interference of the measurements with the external light of the room where the measurements are carried out.

2) The other portion of each mixture was then applied on natural locks of hair at 90% white, for 30 minutes at room temperature (about 20° C.)

At the end of the pause, the lock of hair is rinsed with water and then dried.

The measurements were performed using a Minolta CM2600d colorimeter in the CIE Lab system (illuminant D65, angle 10°, specular component included).

Variation of the Colour of the Mixtures During the Pause

It will be recalled that DE, which in this case evaluates the dyeing power of the mixture, is calculated as follows:

$$DE = [L^{*2} + a^{*2} + b^{*2}]^{1/2}$$

where L*, a* and b* correspond to the values of the coordinates in the CIE L*a*b system.

The higher the value of DE, the more intense the colour of the mixture.

| | Composition according to the invention | | | | Comparative composition | | | |
|---|---|---|---|---|---|---|---|---|
| | L* | a* | b* | DE | L* | a* | b* | DE |
| Reference | 66.62 | −0.5 | 15.46 | — | 66.14 | −0.41 | 9.26 | — |
| 0 min | 64.12 | 0.97 | 12.72 | 3.99 | 57.2 | 0.83 | 11.07 | 9.21 |
| 1 | 65.21 | 0.89 | 13.7 | 2.64 | 57.23 | 0.42 | 11.71 | 9.28 |
| 2 | 64.52 | 0.92 | 14.41 | 2.74 | 56.68 | 0.41 | 12.74 | 10.11 |
| 3 | 63.72 | 0.97 | 15 | 3.28 | 56.1 | 0.45 | 13.67 | 11.00 |
| 4 | 63.05 | 1.02 | 15.44 | 3.88 | 55.58 | 0.48 | 14.39 | 11.77 |
| 5 min | 62.38 | 1.08 | 15.81 | 4.54 | 55.11 | 0.53 | 15.05 | 12.49 |
| 6 | 61.8 | 1.14 | 16.18 | 5.14 | 54.63 | 0.57 | 15.58 | 13.16 |
| 7 | 61.23 | 1.18 | 16.49 | 5.74 | 54.17 | 0.6 | 16.09 | 13.81 |
| 8 | 60.69 | 1.26 | 16.74 | 6.32 | 53.73 | 0.65 | 16.54 | 14.43 |
| 9 | 60.17 | 1.3 | 16.97 | 6.86 | 53.3 | 0.71 | 16.92 | 14.99 |
| 10 min | 59.69 | 1.36 | 17.17 | 7.38 | 52.9 | 0.72 | 17.3 | 15.53 |
| 11 | 59.20 | 1.39 | 17.36 | 7.89 | 52.52 | 0.79 | 17.58 | 16.00 |
| 12 | 58.76 | 1.46 | 17.51 | 8.35 | 52.14 | 0.83 | 17.85 | 16.47 |
| 13 | 58.31 | 1.48 | 17.64 | 8.81 | 51.77 | 0.86 | 18.12 | 16.93 |
| 14 | 57.87 | 1.52 | 17.76 | 9.27 | 51.41 | 0.89 | 18.36 | 17.36 |
| 15 min | 57.44 | 1.56 | 17.86 | 9.71 | 51.07 | 0.95 | 18.55 | 17.75 |
| 16 | 57.04 | 1.59 | 17.96 | 10.12 | 50.73 | 0.97 | 18.72 | 18.13 |
| 17 | 56.64 | 1.62 | 18.01 | 10.51 | 50.41 | 1.02 | 18.86 | 18.48 |
| 18 | 56.27 | 1.65 | 18.06 | 10.88 | 50.08 | 1.03 | 19.03 | 18.85 |
| 19 | 55.87 | 1.66 | 18.12 | 11.28 | 49.77 | 1.05 | 19.15 | 19.18 |
| 20 min | 55.51 | 1.69 | 18.15 | 11.64 | 49.47 | 1.09 | 19.25 | 19.49 |
| 21 | 55.15 | 1.71 | 18.17 | 11.99 | 49.16 | 1.1 | 19.35 | 19.80 |
| 22 | 54.79 | 1.73 | 18.18 | 12.34 | 48.85 | 1.14 | 19.44 | 20.12 |
| 23 | 54.44 | 1.74 | 18.19 | 12.68 | 48.56 | 1.17 | 19.49 | 20.40 |
| 24 | 54.07 | 1.76 | 18.19 | 13.04 | 48.27 | 1.2 | 19.55 | 20.68 |
| 25 min | 53.73 | 1.78 | 18.17 | 13.37 | 47.97 | 1.22 | 19.6 | 20.97 |
| 26 | 53.38 | 1.79 | 18.13 | 13.70 | 47.68 | 1.24 | 19.62 | 21.23 |
| 27 | 53.03 | 1.8 | 18.11 | 14.04 | 47.39 | 1.28 | 19.64 | 21.50 |
| 28 | 52.7 | 1.83 | 18.07 | 14.35 | 47.11 | 1.29 | 19.66 | 21.75 |
| 29 | 52.37 | 1.82 | 18.05 | 14.67 | 46.83 | 1.31 | 19.67 | 22.01 |
| 30 min | 52.04 | 1.83 | 17.97 | 14.98 | 46.53 | 1.34 | 19.65 | 22.26 |

Reference: composition alone (before mixing with the oxidizing composition).

It is found that the coloration of the comparative mixture is far more intense than for the mixture according to the invention.

Coloration of the Locks of Hair

| | L* | a* | b* | DE* |
|---|---|---|---|---|
| Untreated lock of hair | 55.01 | 1.78 | 13.34 | — |
| Composition of the invention | 17.26 | −0.08 | −0.39 | 40.22 |
| Comparative composition | 18.21 | −0.1 | 0.18 | 39.14 |

It is found that the locks of hair coloured with the composition according to the invention are also coloured well (slightly better) than those coloured with the comparative composition.

It is concluded from these two series of results that the compositions according to the invention make it possible to colour the hair at least as well as with the known compositions, while significantly lessening the coloration of the mixture of the composition with the oxidizing composition, as well as its development, during the pause.

The invention claimed is:

1. A dyeing composition for coloring human keratin fibers, comprising at a pH greater than or equal to 8, in a cosmetically acceptable medium,
   at least one oxidative dye precursor;
   at least one cationic surfactant;
   at least one fatty acid ester; and
   at least one fatty alcohol,
wherein the weight ratio of the at least one fatty alcohol to the at least one fatty acid ester is greater than 2 and less than 10.

2. The composition according to claim 1, wherein the composition further comprises at least one direct dye.

3. The composition according to claim 1, wherein the at least one fatty acid ester is chosen from:
   esters of saturated, linear or branched $C_1$-$C_{30}$ monohydric alcohols and saturated or unsaturated, linear or branched $C_{10}$-$C_{30}$ monofunctional fatty acids;
   esters of linear or branched $C_3$-$C_8$ monohydric alcohols and $C_{10}$-$C_{30}$ saturated or unsaturated, linear or branched bifunctional fatty acids; and
   esters of sugars and $C_{10}$-$C_{30}$ fatty acids and diesters of sugars and $C_{10}$-$C_{30}$ fatty acids.

4. The composition according to claim 1, wherein the at least one fatty ester is chosen from esters of saturated, linear, or branched $C_1$-$C_{18}$ monohydric alcohols and saturated or unsaturated, linear or branched $C_{14}$-$C_{18}$ monofunctional fatty acids.

5. The composition according to claim 1, wherein the at least one fatty ester is present in an amount ranging from 0.3 wt. % to 12.5 wt. %, relative to the weight of the composition.

6. The composition according to claim 1, wherein the at least one fatty alcohol is chosen from non-(poly)oxyalkylenated monohydric alcohols having from 14 to 22 carbon atoms and non-(poly)glycerolated monohydric alcohols having from 14 to 22 carbon atoms.

7. The composition according to claim 1, wherein the at least one fatty alcohol is present in an amount ranging from 3 wt. % to 25 wt. %, relative to the weight of the composition.

8. The composition according to claim 1, wherein the at least one cationic surfactant is chosen from:

(i) quaternary ammonium salts of formula (V):

wherein
   $X^-$ is chosen from anions, and
   (1) $R_1$ to $R_3$, which may be identical or different, are each chosen from aliphatic, linear and branched $C_1$-$C_4$ radicals, aryl radicals, and alkaryl radicals, the alkyl radicals optionally having an alkoxy group or an alkyl amide group; and $R_4$ is chosen from linear and branched $C_{16}$-$C_{30}$ alkyl radicals; or
   (2) $R_1$ and $R_2$, which may be identical or different, are each chosen from aliphatic, linear, and branched $C_1$-$C_4$ radicals, aryl radicals, and alkaryl radicals, the alkyl radicals optionally having an alkoxy group, an alkyl amide group, or a $C_1$-$C_4$ hydroxyalkyl group; and $R_3$ and $R_4$, which may be identical or different, are each chosen from linear and branched $C_{12}$-$C_{30}$ alkyl radicals and linear and branched $C_{12}$-$C_{30}$ alkenyl radicals, said radicals optionally having at least one ester group or amide group;

(ii) quaternary ammonium imidazolinium salts of formula (VI):

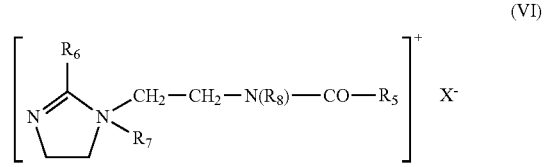

wherein
   $R_5$ is chosen from $C_{12}$-$C_{30}$ alkenyl radicals and $C_{12}$-$C_{30}$ alkyl radicals,
   $R_6$ is chosen from hydrogen, $C_1$-$C_4$ alkyl radicals, $C_{12}$-$C_{30}$ alkenyl radicals, and $C_{12}$-$C_{30}$ alkyl radicals,
   $R_7$ is chosen from $C_1$-$C_4$ alkyl radicals,
   $R_8$ is chosen from hydrogen and $C_1$-$C_4$ alkyl radicals, and
   $X^-$ is chosen from anions;

(iii) quaternary diammonium salts of formula (VII):

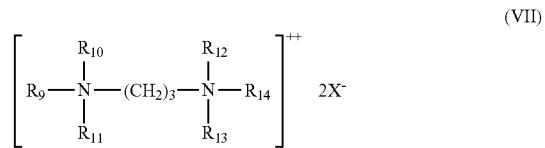

wherein
R$_9$ is chosen from C$_{12}$-C$_{30}$ alkyl radicals and C$_{12}$-C$_{30}$ alkenyl radicals,
R$_{10}$, R$_{11}$, R$_{12}$, R$_{13}$ and R$_{14}$, which may be identical or different, are each chosen from hydrogen and C$_1$-C$_4$ alkyl radicals, and
X$^-$ is chosen from anions; and
(iv) quaternary ammonium salts comprising at least one ester function of formula (VIII):

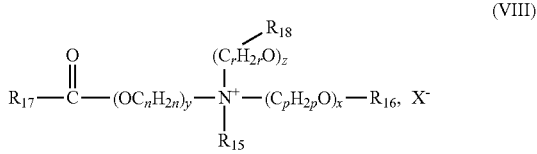

(VIII)

wherein:
R$_{15}$ is chosen from C$_1$-C$_6$ alkyl radicals, C$_1$-C$_6$ hydroxyalkyl radicals, and C$_2$-C$_6$ dihydroxyalkyl radicals;
R$_{16}$ is chosen from R$_{19}$—CO— radicals and R$_{20}$, wherein R$_{20}$ is chosen from linear and branched C$_1$-C$_{22}$ alkyl and alkenyl radicals and hydrogen;
R$_{18}$ is chosen from R$_{21}$—CO— radicals and R$_{22}$, wherein R$_{22}$ is chosen from linear and branched C$_1$-C$_6$ alkyl and alkenyl radicals and hydrogen;
R$_{17}$, R$_{19}$ and R$_{21}$, which may be identical or different, are each chosen from linear and branched C$_{12}$-C$_{22}$ alkyl radicals and linear and branched C$_{12}$-C$_{22}$ alkenyl radicals;
n, p and r, which may be identical or different, are each chosen from integers ranging from 2 to 6;
y is chosen from integers ranging from 1 to 10;
x and z, which may be identical or different, are each chosen from integers ranging from 0 to 10; and
X$^-$ is chosen from organic complex anions, organic simple anions, inorganic simple anions, and inorganic complex anions;
provided that the sum of x+y+z ranges from 1 to 15, and when x has a value 0 then R$_{16}$ is R$_{20}$ and when z has a value 0 then R$_{18}$ is R$_{22}$.

9. The composition according to claim 1, wherein the at least one cationic surfactant is chosen from cationic surfactants of formula (V).

10. The composition according to claim 1, wherein the at least one cationic surfactant is present in an amount ranging from 0.01 wt. % to 25 wt. %, relative to the weight of the composition.

11. The composition according to claim 1, wherein the weight ratio of the at least one fatty alcohol to the at least one fatty ester ranges from 3 to 9.

12. The composition according to claim 1, wherein the weight ratio of the at least one fatty alcohol to the at least one cationic surfactant is greater than or equal to 1.

13. A ready-to-use composition comprising a dyeing composition and at least one oxidizing agent, wherein the dyeing composition comprises at a pH greater than or equal to 8, in a cosmetically acceptable medium,
at least one oxidative dye precursor;
at least one cationic surfactant;
at least one fatty acid ester; and
at least one fatty alcohol,
wherein the weight ratio of the at least one fatty alcohol to the at least one fatty acid ester is greater than 2 and less than 10.

14. The composition according to claim 1, wherein the composition has a pH ranging from 8 to 12.

15. A method for coloring human keratin fibers comprising applying a ready-to-use composition to dry or damp keratin fibers, the ready-to-use composition comprising a dyeing composition and at least one oxidizing agent, wherein the dyeing composition comprises at a pH greater than or equal to 8, in a cosmetically acceptable medium,
at least one oxidative dye precursor;
at least one cationic surfactant;
at least one fatty acid ester; and
at least one fatty alcohol,
wherein the weight ratio of the at least one fatty alcohol to the at least one fatty acid ester is greater than 2 and less than 10.

16. A method for coloring human keratin fibers comprising applying a dyeing composition to dry or damp keratin fibers, in the presence of an oxidizing agent, wherein the oxidizing agent may be applied before or after said dyeing composition, without intermediate rinsing, and wherein the dyeing composition comprises at a pH greater than or equal to 8, in a cosmetically acceptable medium,
at least one oxidative dye precursor;
at least one cationic surfactant;
at least one fatty acid ester; and
at least one fatty alcohol,
wherein the weight ratio of the at least one fatty alcohol to the at least one fatty acid ester is greater than 2 and less than 10.

17. A device comprising a first compartment, comprising a composition comprising at least one oxidative dye precursor, at least one cationic surfactant, at least one fatty acid ester, and at least one fatty alcohol, and a second compartment comprising at least one oxidizing agent, wherein the weight ratio of the at least one fatty alcohol to the at least one fatty acid ester is greater than 2 and less than 10.

* * * * *